United States Patent [19]
Hecht et al.

[11] Patent Number: 5,578,578
[45] Date of Patent: *Nov. 26, 1996

[54] OPHTHALMIC SOLUTIONS

[75] Inventors: Gerald Hecht; Ole J. Lorenzetti, both of Fort Worth, Tex.

[73] Assignee: Alcon Laboratories, Inc., Fort Worth, Tex.

[*] Notice: The portion of the term of this patent subsequent to Apr. 25, 2012, has been disclaimed.

[21] Appl. No.: 425,132

[22] Filed: Apr. 19, 1995

Related U.S. Application Data

[63] Continuation of Ser. No. 977,312, Nov. 16, 1992, Pat. No. 5,409,904, which is a continuation of Ser. No. 553,924, Jul. 17, 1990, abandoned, which is a continuation-in-part of Ser. No. 95,601, Sep. 10, 1987, abandoned, which is a continuation of Ser. No. 899,167, Aug. 22, 1986, abandoned, which is a continuation of Ser. No. 671,042, Nov. 13, 1984, abandoned.

[51] Int. Cl.$^6$ ..................................................... A01N 43/04
[52] U.S. Cl. ................................................................ 514/23
[58] Field of Search .................................................. 514/23

[56] References Cited

U.S. PATENT DOCUMENTS

| | | | |
|---|---|---|---|
| 4,141,973 | 2/1979 | Balazs | 424/180 |
| 4,328,803 | 5/1982 | Pape | 128/276 |
| 4,443,432 | 4/1984 | Garabedian et al. | 424/127 |
| 4,550,022 | 10/1985 | Garabedian et al. | 424/127 |

OTHER PUBLICATIONS

Meyer et al., *J. Biol. Chem.* vol. 107, p. 629 (1934).
Meyer et al., *J. Biol. Chem.* vol. 114, p. 689 (1936).
Balazs, *Fed. Proc.* vol. 17, p. 1086 (1958).
Laurent et al., *Biochem. Biophys. Acta* vol. 42, p. 476 (1960).
Weissman et al., *J. Am. chem. Soc.* vol. 76, p. 1753 (1954).
Meyer, *Fed. Proc.* vol. 17, p. 1075 (1958).
Miller et al., *American Intraocular Implant Society Journal*, vol. 6, No. 1, pp. 13–15 (1980).
Balazs et al., *Mod. Prob. of Ophthal.*, vol. 10, pp. 3–21 (1972).
Hultsch, *Ophthalmology* 87 (7), p. 706 (1980).
Pape et al., *Ophthalmology* 87 (7), p. 699 (1980).
Fechner PU: Methylcellulose, A Viscous Cushioning Material in Ophthalmic Surgery. *Transactions of the Ophthalmol. Societies of the UK* 1983, vol. 103 Part 3.
Fechner PU, Fechner MU: Methylcellulose and Lens Implantation. *British J. of Ophthalmology* 1983, 67: 259–263.
Fechner PU: Methylcellulose in Lens Implantation. *American Intraocular Implant Society J.* 1977, 3: 180–181.
Fechner PU: Use of Methylcellulose During Lens Implantation. *Am. Intraocular Implant Soc. J.* 1980, 6: 368–369.
Aron–Rosa D, Cohn H., Aron JJ, Bouquety C: Methylcellulose Instead of Healon® in Extracapsular Surgery with Intraocular Lens Implantation. *Ophthalmology* 1983, vol. 90 No. 10:1235–1238.
Mac Rae S, Edelhauser H, Hyndiuk RA, Burd BS, Schultz RO: The Effects of Sodium Hyaluronate, Chondroitin Sulfate, and Methylcellulose on the Corneal Endothelium and Intraocular Pressure. *American Journal of Ophthalmology* 1983, vol. 95 No. 3: 332–341.
Smith GS, Lindstrom RL, Miller RA, Hazel S, Skelnik D, William P: Safety and Efficacy of 2% Methylcellulose in Cat and Monkey Cataract–Implant Surgery. *American IntraOcular Implant Society J.* 1984, 10: 160–163.

*Primary Examiner*—Paul J. Killos
*Attorney, Agent, or Firm*—Jeffrey S. Schira

[57] ABSTRACT

Disclosed are solutions useful in surgery comprising a viscous or viscoelastic substance in an aqueous vehicle which is characterized as physiologically compatible; also disclosed are methods of using such solutions, implanting such viscous or viscoelastic substances, while minimizing the traumatic effect of surgery at the cellular level.

4 Claims, No Drawings

OPHTHALMIC SOLUTIONS

This is a continuation of U.S. patent application Ser. No. 07/977,312 filed Nov. 16, 1992, U.S. Pat. No. 5,409,904 which is a continuation of U.S. patent application Ser. No. 07/553,924 filed Jul. 17, 1990 and which is a continuation in part of U.S. patent application Ser. No. 07/095,601 filed Sep. 10, 1987 (now abandoned), which is a continuation of U.S. patent application Ser. No. 07/899,167, filed Aug. 22, 1986 (now abandoned), which is a continuation of U.S. patent application Ser. No. 07/671,042 filed Nov. 13, 1984 (now abandoned.)

BACKGROUND OF THE INVENTION

This invention relates to compositions useful in surgery which contain a viscous or a viscoelastomeric substance or mixture of substances, such as: glycosaminoglycans, such as hyaluronic acid and salts thereof; chondroitin sulfate, alginic acid, polymannuronic acid, polyglucuronic acid and other polyglycuronic acids, mucopolysaccarides, polynucleic acids, polynucleosides, polynucleotides, polydeoxynucleic acids, polydeoxynucleosides, polydeoxynucleotides, polyamino acids, collagen and modified collagen, modified cellulose such as: methylcellulose, hydroxyethylcellulose, hydroxypropylcellulose, and hydroxypropylmethylcellulose, polyvinyl pyrrolidone, polyvinyl alcohol, polyethyleneimine, polyhydroxyethyl methacrylate and other acrylic or methacrylic acid polymers, and the like, in a physiologically compatible solution designed to minimize the traumatic effects of surgery at the cellular level, This Invention also relates to methods for conducting surgery, especially ocular surgery, which comprise administration of such compositions. The foregoing "equivalents" of hyaluronic acid are not publicly known, and constitute distinct embodiments of the present invention.

Hyaluronic acid, a preferred and representative viscoelastic substance for the compositions of the present invention, is a naturally occurring high viscosity glycosaminoglycan having alternating $\beta$1-3 glucuronidic and $\beta$1-4 glucosminidic bonds. The molecular weight of this material is generally within the range of 50,000 to 8,000,000, although there are reports of molecular weights as high as 13,000,000 depending on the source, method of isolation and method of determination. It is found in animal tissue, e.g., umbilical cord, skin, vitreous humour, synovial fluid, rooster combs, and can be obtained from fermentation via Groups A and C hemolytic streptococci.

The isolation and characterization of hyaluronic acid is described in Meyer, et al., *J. Biol. Chem.* 107, 629 (1934); *J. Biol. Chem.* 114, 6589 (1936); Balase, *Fed. Proc.* 17, 1086 (1958); and Laurent, et al., *Biochem, Biophys. Acta* 42. 476 (1960). The structure of hyaluronic acid was elucidated by Weissman, et al., *J. Am. Chem. Soc.* 76, 1753 1954), and Meyer, *Fed. Proc.* 17, 1075 (1958).

Hyaluronic acid and its aforementioned equivalents are useful therapeutic injection materials because of their non-inflammatory response and physical properties of being viscous and viscoelastic. Hyaluronic acid is a natural component of the humours of the eye. Thus, hyaluronic acid approaches the ideal implant material when conducting eye surgery, which involves displacement or removal of vitreous and aqueous humours. The above listed natural, semisynthetic, and synthetic equivalents of hyaluronic acid behave similarly. Such materials are readily available.

U.S. Pat. No. 4,141,973 to Balase describes an ultrapure hyaluronic acid composition for use in ocular surgery. This composition is essentially a 1.0 weight percent solution of the sodium salt of hyaluronic acid dissolved in an aqueous physiological buffer.

There is also available commercially, under the trademark "HEALOX," a physiologically buffered 1.0 weight percent solution of sodium hyaluronate. Literature which discusses this product states that the product does not increase intraocular pressure postoperatively in humans and that it has been used in anterior segment eye surgery, Miller, et al., *American Intraocular Implant Society Journal*, Vol. 6, No. 1, pp. 13–15 (1980). This product is also discussed, for example, in U.S. Pat. No. 4,328,803; wherein it is also stated that the intracameral dilution of "HEALON" with balanced salt solution at the end of the ophthalmic surgical procedure eliminated postoperative pressure elevation, Hyaluronic acid or the commercially available sodium hyaluronate product have been reported in various publications. Thus, in a publication by Balase, et al, *Mod. Prob. of Ophthal.*, Vol. 10, pp. 3–21, 1972, the authors discuss hyaluronic acid and replacement of vitreous and aqueous humours, including the observation that the kinematic viscosity of hyaluronic acid Jelly dissolved in physiologically balanced salt solution may be used. In an article by Hultsch, *Ophthalmology* 87(7), p. 706, 1980, there is a discussion of the scope of hyaluronic acid as an experimental intraocular implant. In a publication by Pape, et al., *Ophthalmology* 87(7), p. 699, 1980, there is a report of the use of sodium hyaluronate in human anterior segment surgery in a wide spectrum of procedures. The authors conclude that the product is safe and facilitates the outcome of surgery, and also results in significantly decreased endothelial cell loss. The authors reported that the product is a viscoelastic jelly manufactured by Pharmacia Company, Inc. It is said to have a viscosity of over 400,000 times that of a balanced salt solution.

A substantial amount of additional work has been done to evaluate the effects of sodium hyaluronate in ocular surgery. This work has been reported, for example, in ARVO Abstracts (1983, 1984) by Meyer, et el., and by McCulley, et el. These abstracts are concerned with the in vitro evaluation of the corneal endothelium after exposure to hyaluronate as well as the tolerance limits therefor.

While substantial work has been done relative to the use of hyaluronic acid (primarily as the sodium salt which is sold commercially for eye surgery), there remains a need in the art for hyaluronic acid and other viscoelastic compositions and methods of administration of such compositions which provide even greater improvements in the compatiblity of such viscous and viscoelastic implants. The present invention meets this need.

It is accordingly an object of the invention to provide novel compositions of matter for use in surgery, especially ocular surgery.

A further object of the invention is to provide compositions comprising a viscous or a viscoelastic material, such as hyaluronic acid or an alkali metal salt thereof, in a physiologically compatible solution, and to provide methods for the administration of such compositions during surgery, especially ocular surgery.

In satisfaction of the foregoing objects, this invention provides a composition of matter useful in surgical manipulations and as an implant material which comprises a solution of hyaluronic acid or an alkali metal salt thereof, or a functional equivalent thereof, such as those viscous and viscoelastic materials representatively listed above, and a physiologically compatible salt solution; said salt solution having a pH of between 6.8 and 8.0 and an osmolality of between 250 and about 350 mOsm/kg and comprising sodium ions, potassium ions, calcium ions, magnesium ions, bicarbonate ions, dextrose and glutathione or the equivalent amount of reduced glutathione, or other suitable sulfhydryl containing compound either in its reduced or oxidized form.

The present invention also provides a method for conducting surgery, e.g., ocular surgery, which comprises implantation or administration of the compositions of the present invention for mechanical purposes or for functional replacement of withdrawn humour, wherein the physiologically compatible salt solution vehicle provides the necessary environment to minimize the traumatic effects of surgery at the cellular level by maintaining, inter alia, the function of intracellular respiratory enzymes.

DETAILED DESCRIPTION OF THE INVENTION

Any surgical invasion invariably entails cell loss. The need to keep cell loss to a minimum is particularly crucial during any surgical procedure performed on delicate and irreplaceable tissues, such as the tissues of neural, renal or ophthalmic function. In fact, these concerns are appropriate for any surgical procedure which substantially overwhelms the target tissue, however brief the time.

With respect to the eye as a target tissue, the cornea is comprised of five layers: the epithelium, Bowman's membrane, the stroma, Decemat's membrane, and the endothelium. The endothelial layer is particularly vulnerable to trauma, as the endothelial cells are infrequently, if ever, replaced as a normal process in adult life. The endothelium is principally responsible for the maintenance of the proper state of hydration of the stromal layer. The stromal layer has a tendency to imbibe fluid, a tendency which is counterbalanced by outward fluid transport via the endothelium. If the proper fluid balance is not maintained in the stromal layer, the cornea thickens and the characteristic transparency of the cornea is lost. Accordingly, cell loss or damage in the endothelial layer will result in decreased vision. Failure of the endothelium to perform its fluid transport function for short periods of time will result in corneal thickening and visual clouding. Because of the importance, and the vulnerability, of the endothelial layer, it is necessary during eye surgery, such as cataract and retinal surgery or corneal transplants, to make provision for the protection of the endothelial cells.

A significant factor causing cell loss during tissue scission (surgery) is the traumatic change in environment. Exposure to the atmosphere or to a foreign wetting solution presents a far different, and possibly hostile environment for the cells. Similarly, exposure to neat aqueous solutions of, for example, hyaluronic acid, presents a challenge for survival to the involved cells. To simulate the natural cellular environment and thereby to prevent cell damage, tissue exposed during surgery is frequently irrigated with solutions which attempt to approximate natural body fluids. The value of bathing eye tissue during surgery to prevent cell damage has long been recognized. For internal ocular tissues, such as the endothelium, the aqueous humor is the natural bathing fluid and hence an ophthalmic irrigating solution to protect the endothelium should resemble the aqueous humour as closely as possible.

As pointed out above, the present invention provides a physiologically compatible solution comprising the viscous or viscoelastomeric substance of choice, such as, hyaluronic acid or its alkali metal salts, or a synthetic or semisynthetic equivalent thereof. It has been found that the resulting compositions minimize the trauma of surgery at the cellular level. For purposes of representative disclosure, the following comments will be directed to compositions comprising hyaluronic acid, a preferred component; although it is understood that the disclosure is applicable to other disclosed viscous and viscoelastomeric polymers.

Hyaluronic acid, or its alkali metal or ammonium salt derivatives are generally available as a gel-like material. For use in the present invention, it is incorporated into the physiologically compatible balanced salt solution in an amount of about 0.1 to 5.0 weight percent. The hyaluronic acid may be present as the free acid, the sodium salt, the potassium salt, the ammonium salt, or mixtures thereof. When combined with the physiologically compatible balanced salt solution, the resulting solution will have an osmolality of about 200 to 600 mOsm/kg and a pH of from about 5.5 to 8.5. The nature of such physiologically compatible balanced salt solutions is further defined below.

The solutions of the present invention provide an improvement in keeping the corneal endothelium viable during surgery, particularly an improvement over the phosphate buffer saline vehicles utilized in the commercial hyaluronic acid products of the prior art.

The compositions of the present invention are especially useful in ocular surgery, such as, implantation of intraocular lenses, anterior segment surgery where protection of the corneal endothelium is required, and surgery in the posterior chamber, such as cataract removal, or vitrectomy.

The compositions of this invention are also useful in other types of surgery. Thus, the composition may be useful to improve pathological joint function in man or animal by relieving pain, reducing inflammation or affecting the healing of an intraarticular wound by injection into an affected joint. Further, the compositions can be used to enhance normal joint and tendon function in man or animal by lubricating the joint or tendon against excess stress during movement by introducing the compositions into the synovial space associated with the joint or tendon.

The compositions may also be used to prevent postoperative adhesion which may occur between healing tissues during the normal healing process and also to keep tissues separated. This method comprises introducing the composition into a surgical site, either during surgery or postoperatively.

The physiologically compatible balanced solution which is combined with the hyaluronic acid or alkali metal salt thereof is fully described in previously filed and commonly assigned applications Ser. No. 308,386, filed Oct. 5, 1981 (now U.S. Pat. No. 4,443,432) and Ser. No. 582,564, filed Feb. 22, 1984; the entire contents of these previously filed applications and this U.S. Patent are incorporated herein by reference.

The physiologically compatible salt solution in its broad aspect may be described as comprising sodium ions, potassium ions, calcium ions, magnesium ions, bicarbonate ions, dextrose, and glutathione or other suitable sources of —SH or —S—S—. The salt solution has a pH of between about 6.8 and 8.0 and an osmolality of between 250 and about 350 mOsm/kg.

In a more preferred aspect, the salt solution comprises between about 3 and about 10 mM/L potassium ions, between about 1 and about 4 mM/L magnesium ions, between about 10 and about 50 mM/L bicarbonate ions, between about 2 and about 10 mM/L dextrose, and between about 0.03 and about 0.5 mM/L oxidized glutathione or the equivalent amount of reduced glutathione, and said solution having a pH of between about 6.8 and about 8.0 and an osmolality of between 250 and 350 mOsm/kg.

A preferred composition according to the invention will contain about 0.1 to 5.0 weight percent of hyaluronic acid (molecular weight from about $0.7 \times 10^6$ to about $2.0 \times 10^6$) as the sodium, potassium or ammonium salt, in the following salt solution:

| Component | Amount (wt. %) |
| --- | --- |
| Sodium Chloride | 0.01 to 1.0 |
| Potassium Chloride | 0.01 to 1.0 |
| Dried Sodium Phosphate | 0.01 to 1.0 |
| Calcium Chloride | 0.01 to 1.0 |
| Magnesium Chloride | 0.01 to 1.0 |
| Dextrose | 0.01 to 1.0 |
| Glutathione (—SH or —S—S—) | 0.005 to 0.5 |
| Sodium Bicarbonate | 0.01 to 1.0 |
| Sodium Hydroxide or Hydrochloric Acid | To Adjust pH |
| Purified Water | QS |
| Osmolality | 200–600 mOsm/kg |
| pH | 5.5–8.5 |

Other preferred compositions are prepared using the previously disclosed viscous or viscoelastic substances, alone or in combination, in place of the hyaluronic acid component.

The final product may be in the form of a single solution (or colloidal gel), two solutions which are combined prior to use, or as products wherein the hyaluronic acid component, or its equivalent, is present as a lyophilized solid which is solubilized by companion solutions prior to use.

As described in the above-mentioned applications and U.S. Patent, salt solutions of this type are preferably provided as two-part solution systems which include a basic solution and an acidic solution. The composition and concentration of the two solutions are such that they are individually stable and may be stored separately for long periods. When mixed together the two solutions form a tissue irrigating solution that may be used for surgery during the next 24 hours. The mixed solution is especially useful for ocular surgery as it contains the necessary factors to maintain endothelial cell integrity and corneal thickness during ocular surgery. It is further found that the same factors are important in maintaining the stability of other sensitive tissues, including nerve tissue. The combined solution contains the necessary ions for tissue stability, $Ca^{++}$, $Mg^{++}$, $Na^+$, $K^+$ and $Cl^-$ in a bicarbonate-phosphate buffer as well as oxidized glutathione and dextrose. As used herein, "glutathione" refers to either the oxidized form of glutathione (GSSG) or the reduced form (GSH). Irrespective of the form used to prepare the solution, the glutathione will be in its oxidized form in the final mixed solution to avoid confusion in labeling, and the solutions will generally be prepared with oxidized glutathione. The solution may also contain adenosine. The hyaluronic acid component, or equivalent, may appear in either the basic or the acidic solution.

Two Part Solution Preparation

As mentioned above, the final product of the present invention may exist as two solutions, either of which may contain the viscous or viscoelastic substance of choice, which solutions are mixed prior to use; or the final product may be initially formulated as a single solution. Also mentioned were product embodiments wherein the viscous or vascoelastic substance was represented as a solid to be hydrated prior to use. All such acts of combination prior to use are achieved through procedures and packaging designs which assure product sterility through ultimate use.

The most preferred product form is the single solution. However, for purposes of disclosure it is simplest to describe preparation of the two solutions, according to the teaching of the above-incorporated by reference U.S. Patent and pending U.S. Patent Application. These solutions are then combined. The viscous or viscoelastic substance may be added to either solution prior to forming the single solution, or it can be added to the single, combined solution. The following paragraphs give an accounting of this sequence. It is understood, however, that for final embodiments of the present invention comprising a single solution the solutions need not follow the following sequence, but may be created initially as a single, unitary product.

The final solution contains from about 130 to about 180 mM/L $Na^+$, from about 3 to about 10 mM/L $K^+$, from about 1 to about 5 mM/L $Ca^{++}$, from about 0.5 to about 4 mM/L $Mg^{++}$, and from about 130 to about 210 mM/L $Cl^-$. To maintain osmotic stability of the cells, the osmolality is between about 250 and about 350 mOsm, and is preferably about 290 to 320 mOsm. So as to closely match the physiological pH of 7.4, the pH of the final irrigating solution is between about 6.8 and about 8.0, and is preferably about 7.2 to 7.8. The bicarbonate concentration in the combined, final solution is between 10 and about 50 mM/L. To stabilize the pH, an additional buffering agent is provided. Preferably, the buffering agent is phosphate provided in sufficient quantity so that the final phosphate concentration of the final solution is between about 1 and about 5 mM/L. The final solution contains between about 2 and about 10 mM/L glucose, between 0.03 and about 0.5 mM/L of oxidized glutathione or the equivalent amount of reduced glutathione, and from about 0.1 to about 5.0 wt. % of the viscous or viscoelastic substance of choice. (One mole of oxidized glutathione is the equivalent of two moles of reduced glutathione.)

The basic solution provides the phosphate and bicarbonate buffering moieties, preferably in the form of dibasic sodium phosphate and sodium bicarbonate. The pH of the basic solution is adjusted to about the physiological pH of 7.4, preferably to between about 7.2 and about 7.8. The pH of a bicarbonate-containing solution is preferably above about 8.0 to prevent decomposition of the bicarbonate. However, the bicarbonate may be stabilized if it is added to a solution with a pH of above about 8 and thereafter adjusted to a pH between 7 and 8. Accordingly, when the basic solution is prepared, $Na_2HPO_4$ is added prior to the addition of $NaHCO_3$ so that $NaHCO_3$ is dissolved in a solution with a pH of between about 8 and about 9. The solution is thereafter adjusted with dilute acid, such as $H_2SO_4$, $H_3PO_4$ or HCl, to the desired final pH of the basic solution. Alternatively, carbon dioxide may be added to adjust the pH.

Potassium and additional sodium are provided in the basic solution in the form of sodium and potassium salts, such as sodium or potassium chloride, sulfates, acetates, citrates, lactates, and gluconates. The sodium and potassium are compatible with all of the moieties present in the final solution, and sodium chloride and potassium chloride may be added to either the acidic or the basic solution or divided between the solutions. However, in view of the fact that the basic solution provides the buffer system, the pH of the final irrigation solution may be more accurately determined if all compatible salts are included in the basic solution.

The acidic solution provides the $Ca^{++}$ in the form of calcium chloride, the $Mg^{++}$ in the form of magnesium chloride, the glutathione and the dextrose. The pH is adjusted to below about 5 to provide long term stability to the dextrose and oxidized glutathione. The acidic solution may be adjusted below a pH of about 5 with a relatively small amount of HCl. The acidic solution is unbuffered. The large volume of buffered basic solution may be adjusted very close to the final pH of the final solution and will be relatively unaffected by the addition of the small volume of the acidic solution. Preferably, the ratio of the basic solution volume to the acidic solution volume is from about 10:1 to about 40:1.

When forming the compositions of the present invention, the viscous or viscoelastic hyaluronic acid or an alkali metal salt thereof, is conveniently dissolved in or mixed with the basic solution, since the basic solution is buffered and the acidic solution is at a pH of below about 5. Mixing of the acidic and basic solutions provides the composition of the invention.

The basic solution and the acidic solution are sterilized and separately bottled or contained under sterile conditions by standard techniques, such as autoclaving, or use of sterilizing filters, but preferably by heat sterilization. Typically, the basic solution, which preferably contains only inorganic moieties, is autoclaved, whereas the acidic solution, which preferably contains the organic components, is microfiltered. To avoid the need for measuring volumes in the hospital, which may introduce possible error and/or contamination, it is highly preferred that particular volumes of the basic and acidic solutions be bottled so that adding the entire content of a container of the acidic solution to the entire content of a container of the basic solution results in the correctly formulated solution.

Precautions to maintain sterility of the solutions and to insure correct mixing of the acidic and basic solutions cannot be overdone. As one method of substantially eliminating the possibility of improper mixing, and to reduce the likelihood of contamination, the solutions may be shipped in a container having a first chamber for the basic solution, an isolated second chamber for the acidic solution, and means to communicate the chambers without opening the container. The use of such containers is known for the shipment of multi-part medical solutions. AS one example, a container may have a lower chamber containing a measured volume of the basic solution separated by a membrane from an upper chamber containing a measured volume of the acidic solution. The container cap may include a plunger means which, when depressed, causes a sharp point or blade depending therefrom to break the membrane. The container is then agitated, as by shaking, to complete the sterile mixing in proper volumes of the acidic and basic solutions.

The proper mixing of the acidic and basic solutions may also be carried out by aseptically removing the acidic solution from its package with a sterile syringe and needle and aseptically adding the acidic solution to the contents of the basic solution package through the rubber stopper. Alternatively, a sterile double-ended needle can be used to transfer the acidic solution to the basic solution by aseptically inserting one end of the needle into the vial containing the acidic solution and then aseptically inserting the other end of the needle into the basic solution package, whereby the vacuum which is maintained therein transfers the acidic solution to the basic solution and the solutions are mixed.

The following examples are presented to illustrate the invention but are not to be considered as limiting thereof. In the examples and throughout the specification, parts are by weight unless otherwise indicated.

EXAMPLE 1

The following composition is prepared by mixing one weight percent of sodium hyaluronate (having an average molecular weight of $1.0 \times 10^6$) in 100 parts of purified water which contains the following components:

| | |
|---|---|
| Sodium Chloride | 1.0 |
| Potassium Chloride | 1.0 |
| Dried Sodium Phosphate | 1.0 |
| Calcium Chloride | 1.0 |
| Magnesium Chloride | 1.0 |
| Dextrose | 1.0 |
| Glutathione | 0.5 |
| Sodium Bicarbonate | 1.0 |

Sodium hydroxide (1N) and hydrochloric acid (1N) are added to adjust the pH to 7.2. The resulting solution is suitable for use during ocular surgery.

Following the procedure of Example 1, substantially equivalent results are obtained when the hyaluronic acid salt component is utilized at the following concentration levels and molecular weights, respectively:

1) 2.0 wt. %, $0.75 \times 10^6$;
2) 2.0 wt. %, $1.0 \times 10^6$;
3) 1.0 wt. %, $1.5 \times 10^6$; and
4) 3.0 wt. %, $0.70 \times 10^6$.

EXAMPLE 2

Separate, sterile, basic, and acidic solutions are made and packaged. A sample of the basic solution and a sample of the acidic solution are mixed, and the combined solution is tested for stability as well as for the ability to maintain the structural integrity and function of rabbit and human endothelium during in vitro perfusion, i.e., simulating intraocular irrigation.

Part I (basic solution) is made by dissolving 2.585 kilograms sodium chloride, 1328.2 grams potassium chloride, and 151.55 grams anhydrous dibasic sodium phosphate in water for injection at about 20° C. Then 918.75 grams of sodium bicarbonate are added and dissolved. Additional water for injection is added to make about 350 kilograms batch weight and 1N HCl is added to adjust the pH to about 7.4. The solution is then passed through a 0.45 micron Millipore filter. To the solution is then added 25 grams of sodium hyaluronate (molecular weight $1.0 \times 10^6$). Each bottle (USP Type I glass) is filled with about 480 ml of solution. Filled bottles are then stoppered, vacuumed and sealed. The sealed bottles are sterilized by autoclaving at 121°–125° C. for up to 30 (thirty) minutes.

Part II (acidic solution) is made by dissolving 385 grams of calcium chloride dihydrate, 500 grams of magnesium chloride hexahydrate, 2300 grams of dextrose, and 516 grams of 95% oxidized glutathione (glutathione disulfide) in water for injection to make a final batch volume of about 100 liters. The solution is then sterile filtered through a 0.22 micron membrane filter and aseptically filled into presterilized 20 ml Type I glass vials and sealed with presterilized rubber stoppers. (Alternatively, the solution can be packaged in Type I glass ampules.)

After adding 20 ml of Part II (acidic solution) to a 480 ml bottle of Part I (basic solution) and mixing, in vitro corneal endothelial perfusion studies are carried out on both rabbit and human donor corneas. The solution is safe and effective and shows a negative swelling rate.

The following Examples 3–6 illustrate compositions which comprise both hyaluronic acid at concentrations of 0.1–5%, with a molecular weight of $0.6 \times 10^6$ to $2.0 \times 10^6$, and either a modified collagen, such as microcystalline collagen, or a modified cellulose, such as methylcellulose, hydroxyethyl cellulose, hydroxypropyl cellulose, hydroxypropyl methylcellulose, or hydroxypropyl ethylcellulose at concentrations of 0.1–5%. These formulations provide both viscoelastic and lubricating properties and can allow for the use of lower hyaluronic acid concentrations, or lower molecular weight hyaluronic acid than prior hyaluronic acid compositions. Compositions with lower hyaluronic acid concentrations, or lower molecular weight hyaluronic acid at comparable concentrations, can have a lower propensity for elevating the intraocular pressure of the dosed eye than known compositions. Also, it can be advantageous to use a lubricating adjunct in addition to a viscoelastic to aid in protecting the endothelium from mechanical injury during surgery.

EXAMPLE 3

| | |
|---|---|
| Hyaluronic acid or salt thereof | 1% |
| Modified cellulose or modified collagen | 1% |
| Sodium chloride | 0.64% |
| Potassium chloride | 0.075% |
| Calcium chloride | 0.048% |
| Magnesium chloride | 0.03% |
| Sodium citrate | 0.17% |
| Sodium acetate | 0.39% |
| Hydrochloric acid and/or sodium hydroxide | q.s. to pH 7–7.2% |
| purified water | q.s. to volume |

EXAMPLE 4

| | |
|---|---|
| Hyaluronic acid or salt thereof | 0.5% |
| Modified cellulose or modified collagen | 2% |
| Sodium chloride | 0.64% |
| Potassium chloride | 0.075% |
| Calcium chloride | 0.048% |
| Magnesium chloride | 0.03% |
| Sodium citrate | 0.17% |
| Sodium acetate | 0.39% |
| Hydrochloric acid and/or sodium hydroxide | q.s. to pH 7–7.2% |
| purified water | q.s. to volume |

EXAMPLE 5

| | |
|---|---|
| Hyaluronic acid or salt thereof | 2% |
| Modified cellulose or modified collagen | 3% |
| Sodium chloride | 0.64% |
| Potassium chloride | 0.075% |
| Calcium chloride | 0.048% |
| Magnesium chloride | 0.03% |
| Sodium citrate | 0.17% |
| Sodium acetate | 0.39% |
| Hydrochloric acid and/or sodium hydroxide | q.s. to pH 7–7.2% |
| purified water | q.s. to volume phosphate buffer |

EXAMPLE 6

| | |
|---|---|
| Hyaluronic acid or salt thereof | 1% |
| Modified cellulose or modified collagen | 2% |
| Sodium chloride | 0.64% |
| Potassium chloride | 0.075% |
| Calcium chloride | 0.048% |
| Magnesium chloride | 0.03% |
| Sodium citrate | 0.17% |
| Sodium acetate | 0.39% |
| Hydrochloric acid and/or sodium hydroxide | q.s. to pH 7–7.2% |
| purified water | q.s. to volume phosphate buffer |

We claim:

1. An ophthalmic solution comprising a therapeutically effective amount of a viscous or viscoelastic material selected from the group consisting of collagen, modified collagen and modified cellulose and combinations thereof in a physiologically compatible salt solution, the salt solution containing bicarbonate ions.

2. The solution of claim 1 wherein the physiologically compatible salt solution further contains sodium, potassium, calcium, and magnesium ions.

3. The solution of claim 1 wherein the viscous or viscoelastic material comprises hydroxypropylmethylcellulose.

4. The solution of claim 1 wherein the bicarbonate ions are present in a concentration of between about 10 mM/L and about 50 mM/L.

* * * * *